United States Patent [19]

Heuscher et al.

[11] Patent Number: 4,965,726

[45] Date of Patent: Oct. 23, 1990

[54] CT SCANNER WITH SEGMENTED DETECTOR ARRAY

[75] Inventors: Dominic J. Heuscher, Aurora; Rodney A. Mattson, Mentor, both of Ohio

[73] Assignee: Picker International, Inc., Highland Hts., Ohio

[21] Appl. No.: 260,403

[22] Filed: Oct. 20, 1988

[51] Int. Cl.$^5$ ............................................. G06F 15/42
[52] U.S. Cl. ............................ 364/413.19; 364/413.13
[58] Field of Search ......................... 364/413.13, 413.19

[56] References Cited

U.S. PATENT DOCUMENTS

| | | | |
|---|---|---|---|
| 3,973,128 | 8/1976 | LeMay | 250/445 |
| 4,150,292 | 4/1979 | Ter-Pogossian | 378/20 |
| 4,160,911 | 7/1979 | Hounsfield | 250/445 |
| 4,176,280 | 11/1979 | Greschat et al. | 250/445 |
| 4,187,430 | 2/1980 | Schmidt | 250/445 |
| 4,193,001 | 3/1980 | Liebetruth et al. | 250/415 |
| 4,247,774 | 1/1981 | Brooks | 253/367 |
| 4,384,209 | 5/1983 | Wagner et al. | 378/6 |
| 4,559,639 | 12/1985 | Glover et al. | 378/19 |
| 4,686,692 | 8/1987 | DeMeester et al. | 378/4 |
| 4,747,117 | 5/1988 | Albrecht et al. | 378/19 |
| 4,752,879 | 6/1988 | Brunnett | 364/413.21 |

Primary Examiner—Jerry Smith
Assistant Examiner—Gail O. Hayes
Attorney, Agent, or Firm—Fay, Sharpe, Beall, Fagan, Minnich & McKee

[57] ABSTRACT

A plurality of segmented radiation sensitive arrays (30) receive radiation from a radiation source (16) which has transversed an examination region (14) of a CT scanner (10). Each array includes a plurality of rows (A, B, C) of radiation sensitive cells, e.g. photodiodes, which produce an electrical signal indicative of the intensity of radiation received. Within each of the rows, there are larger cells and smaller cells. The electrical signals from each of the plurality of cells within each row are serialized (34) and amplified (36A, 36B, 36C). Selected combinations of the electrical signals from the various rows and larger and smaller elements within each row are combined (46) and reconstructed (50) into an image representation (52) for display on a video monitor or the like.

20 Claims, 3 Drawing Sheets

CT SCANNER WITH SEGMENTED DETECTOR ARRAY

BACKGROUND OF THE INVENTION

The present invention pertains to the art of medical diagnostic imaging, particularly computerized tomographic (CT) scanners. The invention finds application in conjunction with volumetric, medical diagnostic imaging and will be described with particular reference thereto. However, it is to be appreciated that the invention also relates to single slice imaging, quality control examinations, and the like.

Heretofore, CT scanners have included a plurality of discrete radiation detectors arranged in a ring or rotatable ring segment around a patient examination region. Each discrete detector included a scintillation crystal which received radiation traversing a selected slice of a patient in the image region and converted the x-ray energy into light. A solid state photodiode or vacuum photomultiplier tube converted the light emitted by the scintillation crystal into electrical signals indicative of the intensity of emitted light, hence, the intensity of received radiation. By providing two rings of photodiodes or photomultiplier tubes back-to-back, two slices have been collected concurrently.

The use of discrete radiation detectors, such as photodiodes or photomultiplier tubes, has several drawbacks. First, installation is labor-intensive and expensive. Further, the prior art scintillation crystal/photodiode or photomultiplier tube assemblies tend to be relatively large and bulky which limits the density or number which may be disposed around the scan circle. The number of discrete crystal/photodiode units may also be limited by the sampling frequency and data processing capacity of the scanner.

Thick slices created when the entire face of each discrete detector received radiation suffered from visible partial volume effects. Narrow slices were created by screening part of the detector from receiving radiation. The flux limitations of the tubes required slower narrow slice scan times which lowered scanner throughput.

The present invention overcomes the above referenced problems and others.

SUMMARY OF THE INVENTION

In accordance with the present invention, a CT scanner is provided. A radiation source rotates a beam of radiation about an examination region. A plurality of segmented radiation sensitive arrays receive radiation that has traversed the examination region from the source and produces electrical signals indicative of the intensity of received radiation. An image reconstruction means reconstructs an image representation from the electrical signals.

In accordance with a more limited aspect of the present invention, each radiation sensitive array includes a regular grid of detectors mounted to a single substrate. In one dimension along the grid, there are a plurality of detectors disposed parallel to an axis of rotation to define a plurality of slices and a plurality of detectors extending radially around the examination region for receiving a plurality of rays of radiation within each slice.

In accordance with a more limited aspect of the present invention, the detector grids may be composed of solid state photodiodes electrically linked on the same substrate to a CCD array or an FET array.

In accordance with another aspect of the present invention, the radiation detectors of the array vary in size. The detectors may vary in length to vary the width of the slice information. Also, the detectors may vary in width along the circumference of the scan circle to vary the resolution/optical efficiency.

One advantage of the present invention resides in the generation of volumetric data. The volume may be defined from multiple fan beam projections acquired simultaneously from an x-ray source moving in successive circular paths as the patient table is incremented. Alternatively, the x-ray source may move in a continuous circular path as the table also moves continuously. This results in x-rays traversing multiple helical paths around the patient or object. Because multiple projections are being collected simultaneously, the x-ray flux utilization is increased and the total examination period for a given volume is significantly reduced.

Another advantage of the present invention resides in its flexibility and imaging versatility. Multiple detectors can be grouped to maintain high photo efficiency while reducing the amount of data that has to be collected and processed. This can be done with a minimal reduction in resolution. If detectors are grouped in the axial direction, partial volume artifacts are significantly reduced over current scans of the same slice thickness.

Other advantages include being able to achieve multiple thin slices of more than one thickness. Because these slices are adjacent or nearly adjacent to each other, the off-plane effects are minimized.

Still further advantages of the present invention will become apparent upon reading and understanding the following detailed description of the preferred embodiments.

BRIEF DESCRIPTION OF THE DRAWINGS

The present invention may take form in various components and arrangements of components and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
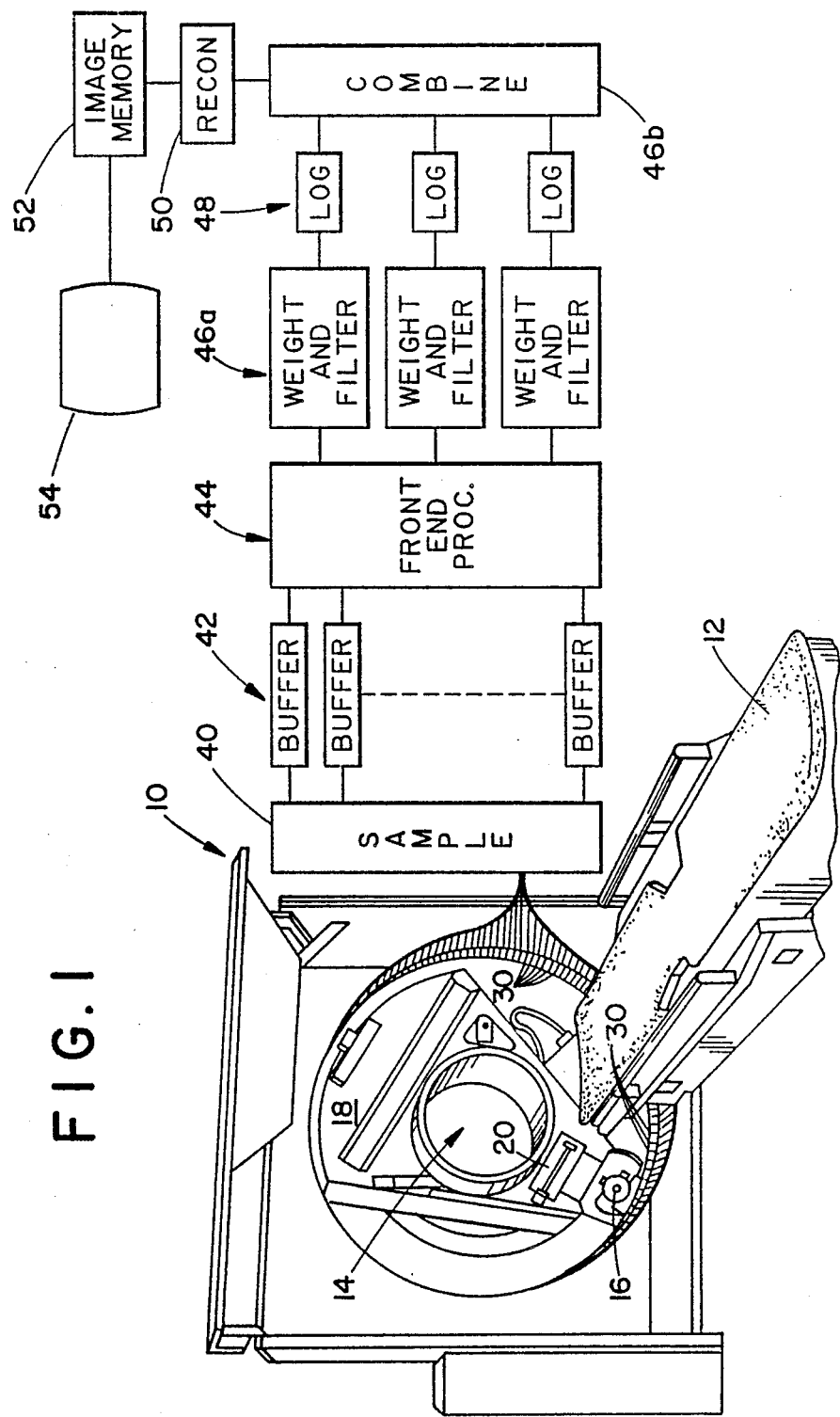
FIG. 1 is a diagrammatic illustration of a CT scanner in accordance with the present invention.

With reference to FIG. 1, a CT scanner 10 selectively images cross sectional slices of a region of a patient supported on a stationary patient couch 12 within a scan circle or patient aperture 14. In some applications, the patient couch is incremented to take a plurality of parallel slices. In another embodiment, the couch moves continuously such that the patient is scanned along helical paths. An x-ray tube 16 for emitting a fan-shaped beam of radiation toward and spanning the scan circle 14 is mounted to a rotatable gantry 18. Alternatively, a multispot x-ray tube may be utilized to increase the thickness of the fan beam or generate plural parallel beams.

Figure 2:
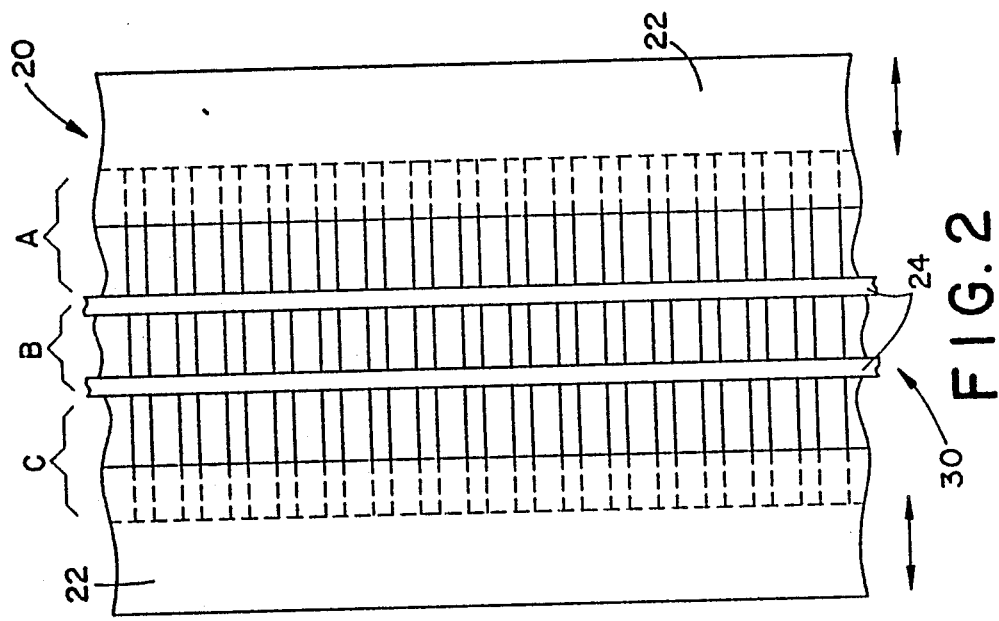
FIG. 2 illustrates a portion of the collimators overlaying the segmented detector arrays.

With reference to FIG. 2, a collimator 20 defines the dimensions of the x-ray beam(s), particularly its width to select the thicknesses of an individual slice or group of slices which are imaged. An outer continuously adjustable collimator 22 sets the overall width of the x-ray beam, i.e. the width of the outer slices. If the outer collimator is closed sufficiently, the outer slices may be eliminated and the center or inner slice(s) can be narrowed. If the halves of the outer collimator are moved independently, one of the outer slices may be eliminated and the other adjusted to a selected width, e.g. the width of the inner slice. An inner collimator 24 selectively narrows the radiation received by the center detectors, i.e. narrows the center or inner slice. In the preferred embodiment, the inner collimator has a fixed profile which is selectively moved into and out of the radiation beam. Optionally, the fixed collimator segments may have selectable profiles such that the center slice collimation is adjustable. Other mechanical slice thickness adjustment or selection devices for the inner and outer slices may, of course, be utilized.

A plurality of segmented detector array modules 30 receive radiation which has traversed the scan circle and provide output signals indicative of the intensity of received radiation. In the preferred embodiment, 128 detector modules each include three segments of 24 photodiodes to define three rings of 2,880 detectors per ring around the scan circle.

Figure 3:
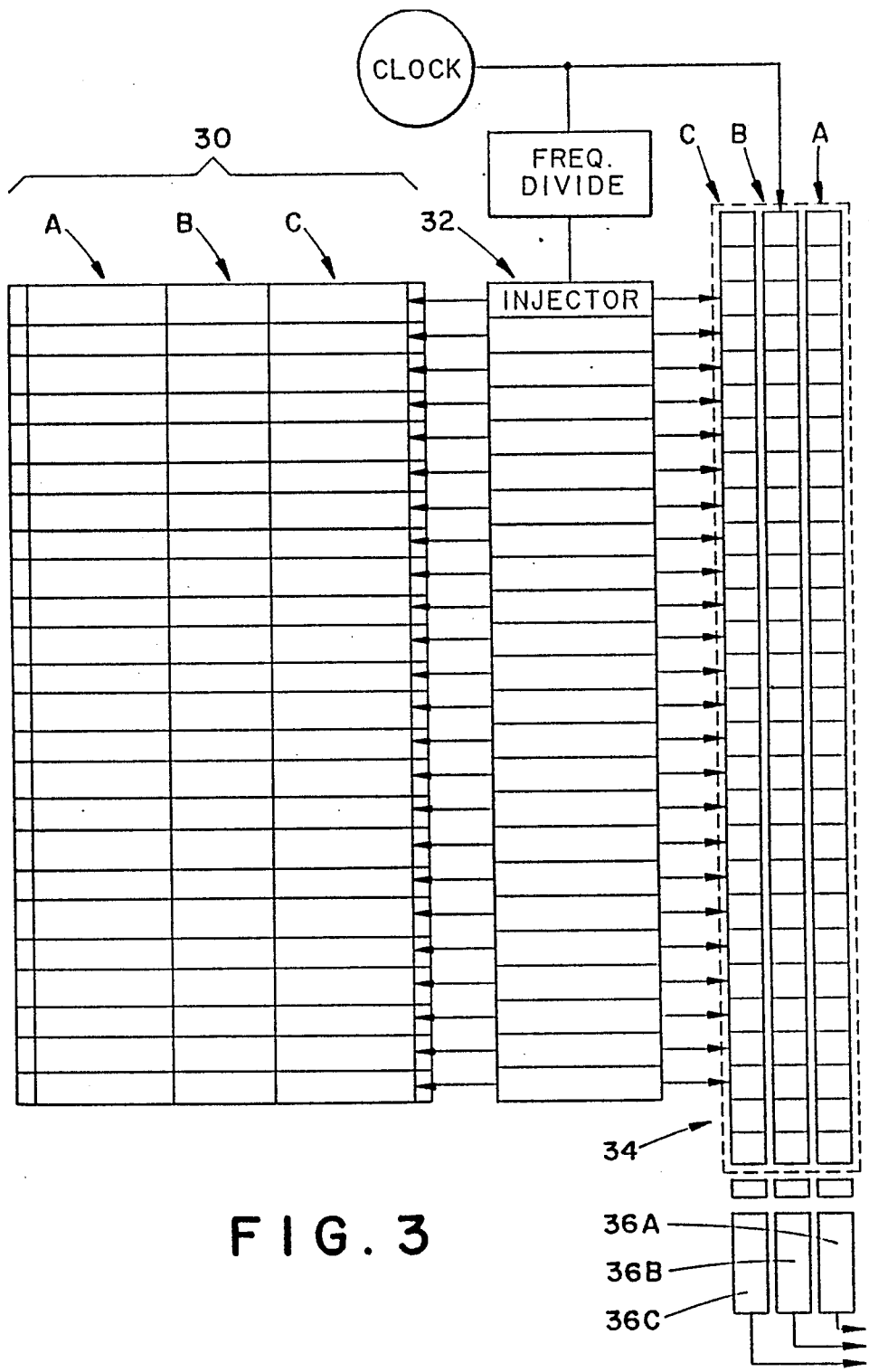
FIG. 3 illustrates a segmented photodiode array in combination with CCD array; and, FIG. 4 is illustrative of a segmented photodiode array in combination with an FET array on a single substrate.

With particular reference to FIG. 3, each detector module includes three rows or segments A, B, C of 24 x-ray sensitive cells each. The cells of row A are labelled A1–A24, etc. Of course, other numbers of rows, such as five or more, may be provided and other numbers of radiation sensitive cells may be provided within each array without departing from the present invention. The center row or segment B preferably is narrower than the side segments A and C. This enables the center segments to have higher resolution or define a narrower slice. By selectively adjusting the collimator 20, the amount of radiation impinging on the outer segments A and C and the amount impinging on inner segments B are selectively adjustable. This enables the slice defined by the outer segments to be the same as the center segment, wider, or narrower. Within each segment, there are a plurality of different width detectors. In the preferred embodiment, wider detectors A1, A3, A5, . . . A23, B1, B3, . . . B23, C1, C3, . . . C23 alternate with narrower detectors A2, A4, A6, . . . A24, B2, B4, . . . B24, C2, C4, . . . C24.

Further to the preferred embodiment, the radiation sensitive cells of the modules 30 are photodiodes. An array of charge injectors 32 periodically, at the sampling interval, recharges each photodiode of the array to a preselected charge level. As radiation impinges on the photodiodes, the charge is dissipated in proportion to the intensity of radiation and the duration of exposure. At the end of each sampling interval when the injectors 32 recharge each photodiode, the injectors provide a like amount of charge to corresponding cells of a CCD array 34. The CCD array 34 has three rows of cells which in FIG. 3 are labelled with the same designation as the corresponding photodiode of the photodiode array 30. The cells of the CCD array may be arranged in a different order than the corresponding diodes of the photodiode array to accommodate the order of data anticipated by downstream processing equipment. In this manner, the CCD array is loaded with charge values indicative of the amount of charge necessary to recharge each photodiode to the preselected charge, hence, the amount of charge dissipated. Optionally, an indication of the charge remaining on each photodiode may be transferred to the CCD array.

After each sampling, the charge values in each cell rows A, B, and C of the CCD array are shifted rapidly to charge amplifiers 36A, 36B, and 36C, respectively. In the 3×24 element array, the charge values are shifted each 1/24th or less of the sampling interval. In this manner, the data from one sampling is converted to serial video signal data and the CCD array is ready to receive new data before the next sampling. If the three rings of detectors are read serially rather than in parallel, the data is clocked out of each row of the CCD array three times as fast, such that all three rows are emptied before the next sampling.

With reference again to FIG. 1, electrical output signals from amplifiers 36A, 36B, and 36C indicative of the amount of radiation received by the photodiodes of each ring are sampled by a sampling means 40. Buffer memories 42 store the sampled data until a front end processor means 44 digitizes the signals and performs digital signal processing operations, as are known in the art. In the illustrated embodiment, each buffer receives data serially from one of the detector rings. A combining means 46 includes an intraring weighting and filtering means 46a for selectively weighting or filtering the data from the different sized detectors of each ring. Algorithm means 48 converts the data to its logarithmic value. In the illustrated embodiment, three logarithmic circuits each process the data from one detector ring.

The combining means 46 further includes an axial combining means 46b for combining data from the plurality of detector rings. In response to the operator selecting an imaging mode, the combining means selects a corresponding combination algorithm. The selected or combined detector data is reconstructed into an image representation by an image reconstruction means 50 such as a convolution and filtered back projection algorithm. The image representation may be stored in one or more image memories 52 for selective display on one or more video monitors 54. Alternately, the image representations may be stored in computer memory, stored on tape, subject to further processing, or the like.

The operator can select various imaging modes including single and multiple slice modes with different resolutions. In the various modes, the outputs of the detectors are combined in various manners, both axially and transversely or processed independently. For example, in one single slice mode, the outputs of each set of corresponding A, B, and C detectors are combined. More specifically, the outer collimator adjusts the outer slice width 22 and the inner collimator 24 sets the width of the center slice. The three rings of detectors receive the radiation and produce output signals which could be used to produce three slices. Unless the center and outside detectors are exposed to the same amount of radiation, the three slices have different resolutions. The corresponding elements of the three slices are weighted to accommodate the different resolutions, summed, averaged, or the like. In an embodiment in which the center detectors are three millimeters wide and the outer ones, four millimeters wide, this single slice technique is applicable to single slices with a width of about three to ten millimeters.

In another single slice embodiment, only the center row of radiation detectors are utilized. The adjustable outer collimators or the fixed inner collimators may be utilized to reduce the width of the single slice below the width of the center detector elements.

In a multiple slice mode, three slices are produced. That is, the data from each of the three rings of elements is processed separately. The center slice has the width of the center row of detector elements or the width defined by the inner collimator. The width of the outer slices is separately adjusted by the outer collimator. For many applications, it is advantageous to have all three slices the same width or resolution. In another multiple slice mode, two overlapping slices are produced. Data from corresponding center detector cells and corresponding detector cells on one of the sides are combined to produce one set of data. Data from the same center detector and corresponding detectors of the other outer ring are also combined to produce a second set of data. The two sets of data, which represent overlapping slices, are processed separately. Again, the width of the slices may be adjusted with the collimator 20.

As yet another alternative, transverse combinations of radiation detector elements can be selected. In a spatially weighted view averaging mode, adjacent detector elements within the same one of rings A, B, and C are combined or weighted with elements of different sizes. This effectively averages the views from which the resultant image is reconstructed. In a filtering mode, the data from adjacent detector elements within each ring is time averaged or weighted. In a view averaging mode, the outputs of adjacent detectors are summed or averaged without filtering or weighting. As yet another alternative, the views that are summed or averaged may be the time filtered or spatially weighted views described above. Various other imaging modes or combinations of these imaging modes may, of course, be selected. The logarithm may be taken earlier or later in the processing stream. Preferably, the log is taken before the axial combination to reduce partial volume effects.

Figure 4:
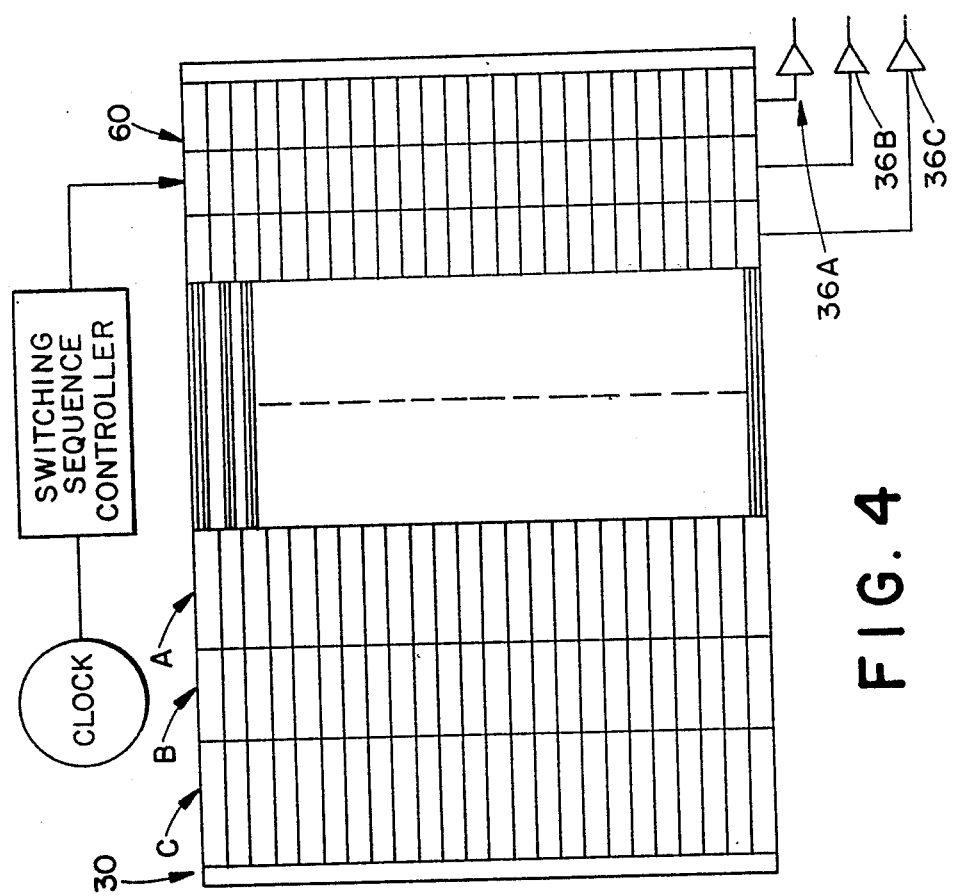

With reference to FIG. 4, in an FET embodiment, the photodiode array 30 is interconnected with an array of FET switches 60. The FETs are each connected with one of the photodiodes for conveying an indication of the conductivity of the sampled photodiode to a corresponding one of output amplifiers 36A, 36B, and 36C. Preferably, an instantaneous voltage across a photodiode and resistor combination is sampled. Optionally, other means besides an FET array or a CCD array may be provided for converting concurrently collected data into serial data signals.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A transmission CT scanner comprising:
   a means for defining an examination region;
   a radiation source means for rotating a beam of radiation about the examination region;
   a plurality of segmented arrays of radiation sensitive cells for receiving radiation which has transversed the examination region from the source means and for producing electrical signals indicative of the received radiation, each segmented array including:
   a common substrate,
   a regular two dimensional grid of solid state radiation sensitive cells formed on the common substrate, the grid having a plurality of rows of radiation sensitive cells in a peripheral direction generally parallel to a circumference of the examination region and a plurality of rows of cells along a longitudinal direction; and,
   an image reconstruction means for reconstructing the electrical signals into an image representation.

2. The scanner as set forth in claim 1 further including:
   a CCD array having a plurality of rows of CCD cells;
   an injector means for transferring charge values from cells of the radiation sensitive array to cells of the CCD array;
   an amplifier connected with each row of CCD cells; and,
   a clock means for serially causing the amplifier to amplify an output from each of the cells in its associated CCD cell row.

3. The scanner as set forth in claim 1 further including an array of FETS for serially connecting the radiation sensitive cells to output amplifiers.

4. A projection radiographic scanner comprising:
   a means for defining an examination region;
   a radiation source means for rotating a beam of radiation about the examination region;
   a plurality of segmented arrays of radiation sensitive cells for receiving radiation which has transversed the examination region form the source means and for producing electrical signals indicative of the received radiation, each of the segmented radiation sensitive arrays includes cells having radiation sensitive faces of a plurality of different sizes; and,
   an image reconstruction means for reconstructing the electrical signals into an image representation.

5. The scanner as set forth in claim 4 wherein each array has a plurality of rows of cells generally longitudinally along the examination region, each longitudinal row of cells including elements of at least two different sizes.

6. A CT scanner comprising:
   a means for defining an examination region;
   a plurality of segmented arrays of radiation sensitive cells mounted peripherally around the examination region, the cells of the plurality of arrays defining at least one peripheral ring of cells around the examination region, each array having a row of radiation sensitive cells lying in the peripheral ring, each row of cells having cells with radiation sensitive faces of one of at least two different sizes in a dimension along the peripheral ring;
   an image reconstruction means for constructing an image representation from electrical signals generated by the arrays.

7. A CT scanner comprising:
   a means for defining an examination region;
   a radiation source means for rotating a beam of radiation about the examination region;
   a plurality of segmented arrays of radiation sensitive cells for receiving radiation which has transversed the examination region from the source means and for producing electrical signals indicative of the received radiation;

a sampling means for sampling the electrical signals from each cell;

a weighting and filtering means for selectively spatially weighting and temporally filtering the sampled electrical signals, the spatial weighting and temporal filtering being adjustable to match the electrical signals to a selected reconstruction algorithm;

a combining means for selectively combining the weighted and filtered electrical signals;

a logarithm means for determining a logarithm of the combined electrical signals, the logarithm means being operatively connected with the combining means; and, an image reconstruction means for reconstructing the electrical signals into an image representation with the selected reconstruction algorithm.

8. A CT scanner comprising:

a means for defining an examination region;

a plurality of segmented arrays of radiation sensitive cells for receiving radiation from the examination region and for producing electrical signals indicative of the received radiation, each of the arrays including radiation sensitive cells of at least first and second sizes;

a plurality of memory means, each memory means storing electrical signals from a preselected subset of cells of each of the plurality of arrays; and, a combining means for selectively combining stored electrical signals from the memory means, the combining means being operatively connected with an image reconstruction means for supplying the combined electrical signals thereto.

9. A CT scanner comprising:

a means for defining an examination region;

a radiation source means for rotating a beam of radiation about the examination region;

a plurality of segmented arrays of radiation sensitive cells for receiving radiation which has traversed the examination region from the source means and for producing electrical signals indicative of the received radiation, each array including a rectangular grid of cells with peripheral cell rows along a peripheral direction parallel to a periphery of the examination region and with longitudinal cell rows transverse thereto; p1 a collimator means for adjustably screening a selective portion of selectable rows of the radiation sensitive cells; and, an image reconstruction means for reconstructing the electrical signals into an image representation.

10. A method of medical diagnostic imaging comprising:

rotating a fan beam of radiation around an object to be imaged;

detecting radiation which has traversed the object with a plurality of segmented arrays, each of the arrays having a two dimensional grid of radiation sensitive cells;

serially reading radiation absorption data from radiation sensitive cells of each array;

combining data from a plurality of cells; and, reconstructing a transverse image representation from the combined, serially read data.

11. The methods set forth in claim 10 further including logarithmically amplifying the combined, serially read data, whereby filtering and resampling of data to accommodate a selected reconstruction algorithm is facilitated.

12. The method as set forth in claim 10 further including logarithmically amplifying the serially read data before the combining step and wherein the combining step includes combining data from longitudinally adjacent cells such that the reconstructed image representation represents an image through a thicker slice of the object, whereby defining a thicker slice from smaller detectors avoids partial volume artifacts.

13. The method as set forth in claim 10 further including logarithmically amplifying the data before the combining step and wherein the combining step includes combining data from peripherally adjacent cells, whereby data is averaged while maintaining geometric efficiency of the cells.

14. A CT scanner comprising:

a means for defining an examination region;

a plurality of segmented arrays mounted in a peripheral ring around the examination region, each array including a common substrate on which a two dimensional array of solid state radiation sensitive cells are deposited, each cell receiving radiation from the examination region and producing electrical signals indicative of said received radiation;

an array of at least one of (a) transistors and (b) charged coupled devices deposited on the common substrate for serially connecting the radiation sensitive cells to output amplifiers, which output amplifiers are also disposed on the common substrate.

15. The scanner as set forth in claim 14 further including a serializing means for generating at least one output signal of serial data values indicative of radiation received by the radiation sensitive cells.

16. The scanner as set forth in claim 15 wherein the serializing means includes a CCD array and a charge injector means connected for transferring charge values indicative of radiation received from the radiation sensitive array to the CCD array, the CCD array, the CCD array being clocked to produce the output signal.

17. The scanner as set forth in claim 15 wherein the serializing means includes an array of FETs on a common substrate.

18. The scanner as set forth in claim 14 wherein the plurality of arrays defines more than two rings of radiation sensitive cells surrounding the scan circle, each ring having more than 2,000 radiation sensitive cells therein.

19. The scanner as set forth in claim 18 wherein the radiation sensitive cells include photodiodes.

20. The scanner as set forth in claim 14 wherein the cells of each array each have a radiation receiving face, a first fraction of the cell faces having a first dimension in one direction and another fraction of the cell faces having a second dimension in said first direction, the second dimension being smaller than the first dimension.

* * * * *

UNITED STATES PATENT AND TRADEMARK OFFICE
CERTIFICATE OF CORRECTION

PATENT NO. : 4,965,726

DATED : October 23, 1990

INVENTOR(S) : Heuscher, et al.

It is certified that error appears in the above-identified patent and that said Letters Patent is hereby corrected as shown below:

On the cover sheet, in section [75] listing the inventors, --Carl J. Brunnett, Willoughby Hills, Ohio-- should be listed as a co-inventor.

Signed and Sealed this

Eighteenth Day of February, 1992

Attest:

HARRY F. MANBECK, JR.

*Attesting Officer*  *Commissioner of Patents and Trademarks*